United States Patent [19]

Cho et al.

[11] Patent Number: 5,063,243

[45] Date of Patent: Nov. 5, 1991

[54] DERIVATIVE OF CAFFEIC ACID AND PHARMACEUTICAL COMPOSITION CONTAINING THE SAME

[75] Inventors: Hidetsura Cho, Osaka; Masaru Ueda, Saitama; Mie Tamaoka, Nara; Mikiko Hamaguchi, Hyogo; Seiitsu Murota; Ikuo Morita, both of Tokyo, all of Japan

[73] Assignee: Suntory, Ltd., Osaka, Japan

[21] Appl. No.: 344,583

[22] Filed: Apr. 28, 1989

[30] Foreign Application Priority Data

Apr. 28, 1988 [JP] Japan .................................. 63-106274
Mar. 8, 1989 [JP] Japan .................................... 1-55867

[51] Int. Cl.$^5$ .................. A61K 31/275; A61K 31/38; C07C 255/34; C07D 333/22
[52] U.S. Cl. ........................... 514/438; 514/445; 514/521; 549/65; 549/77; 558/400; 558/401; 546/330; 548/341
[58] Field of Search ................. 558/401, 400; 549/77; 514/438, 521, 357, 399, 445; 546/330; 548/341

[56] References Cited

U.S. PATENT DOCUMENTS 3,855,301 12/1974 Rizzi .............................. 568/331 X
3,892,777 7/1975 Gruenman et al. ................ 549/441

OTHER PUBLICATIONS

C.A. 75: 151793k, (1971), Gruenman, et al.
C.A. 82: 155799j, (1975), Rizzi.
C.A. 84: 17347a, (1976), Gruenman, et al.
C.A. 84: 105592g (1976), Gruenman, et al.
C.A. 92: 93986p (1980), Rai, et al.
C.A. 92: 1216437b (1980), Preuss, et al.
C.A. 101: 85528e (1984), Manrao, et al.

*Primary Examiner*—Joseph Paul Brust
*Attorney, Agent, or Firm*—Cushman, Darby & Cushman

[57] ABSTRACT

Novel derivatives of caffeic acid of the general formula (I):

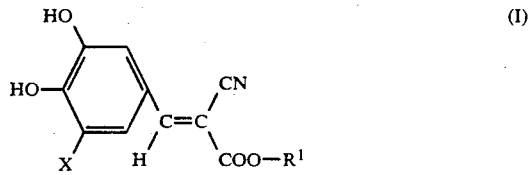

wherein X is hydrogen atom or hydroxy; $R^1$ is hydrogen atom, a straight or branched alkyl or alkenyl having 1 to 20 carbon atoms or a group of the formula:

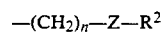

$$-(CH_2)_n-Z-R^2$$

wherein n is an integer of 1 to 10; Z is oxygen atom, vinylene residue or a single bond; and $R^2$ is a substituted or unsubstituted phenyl or heterocyclic residue is provided. These derivatives possess 12-lipoxygenase inhibitory activity and are useful for curing and preventing circulatory diseases. A pharmaceutical composition containing said derivtive is also provided.

5 Claims, No Drawings

DERIVATIVE OF CAFFEIC ACID AND PHARMACEUTICAL COMPOSITION CONTAINING THE SAME

BACKGROUND OF THE INVENTION

The present invention relates to a novel derivative of caffeic acid which possesses 12-lipoxygenase inhibitory activity and is useful for the prevention and remedy of circulatory diseases such as arteriosclerosis, and to a pharmaceutical composition containing said derivative.

PRIOR ART

Leukotriene, which is considered to be a cause of allergic diseases such as asthma, is produced from arachidonic acid via 5-hydroperoxyeicosatetraenoic acid (5-HPETE) which is generated by the action of 5-lipoxygenase and 5-hydroxyeicosatetraenoic acid (5-HETE) as intermediates. On the basis of this fact, a number of compounds exhibiting inhibitory activity against 5-lipoxygenase have been reported in connection with the development of agents for treating circulatory diseases.

On the other hand, it is also known that 12-hydroperoxyeicosatetraenoic acid (12-HPETE) and 12-hydroxyeicosatetraenoic acid (12-HETE) are produced from arachidonic acid by another converting enzyme, 12-lipoxygenase. With respect to the biological activity of these compounds, Tada et al. reported that 12-HETE is related to the outbreak of ischemic heart disease (Cardiovascular Research, vol. 21, No. 8, 551–558, 1987), and Murota et al. reported that 12-HETE exhibited harmful activity against endothelial cells and enhanced the migration of smooth muscle cells in the vascular medial membrane to result in ingravescence of circulatory diseases such as arteriosclerosis and nephritis (Chiryogaku, vol. 13, No. 6, 785–788, 1984).

These facts suggest that compounds capable of inhibiting 12-lipoxygenase may be expected to be useful in the treatment of circulatory diseases; among such compounds baicalein isolated from *Scutellaria baicalensis* have been reported as a naturally occurring compound while the derivatives of tropolone (Japanese Patent Laid-Open No. 228414/1985) and those of naphthalene (Japanese Patent Laid-Open Nos. 251640/1986, 251641/1986 and 251642/1986) have been reported as synthetic compounds. Since their biological activity is not sufficient, however, the development of novel inhibitors is required.

SUMMARY OF THE INVENTION

Taking this situation into consideration, the present inventors completed the present invention by screening a wide range of compounds possessing 12-lipoxygenase inhibitory activity and found that derivatives of caffeic acid of the general formula (I) are as active as or more active than the aforementioned inhibitors against 12-lipoxygenase, and also that these derivatives have low toxicity and that synthesis thereof is easy.

DETAILED DESCRIPTION OF THE INVENTION

According to the present invention, derivatives of caffeic acid of the general formula (I) are provided:

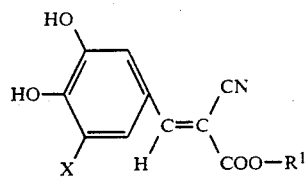

wherein X is hydrogen atom or hydroxy; $R^1$ is hydrogen atom, a straight or branched alkyl or alkenyl having 1 to 20 carbon atoms, or a group of the formula:

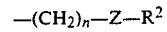

wherein n is an integer of 1 to 10; Z is oxygen atom, vinylene residue or a single bond; and $R^2$ is a substituted or unsubstituted phenyl or heterocyclic residue; as well as their pharmaceutically acceptable salts, and pharmaceutical compositions containing said derivative. Examples of $R^1$ and the general formula (I) include, for instance, methyl, ethyl, propyl, isopropyl, n-butyl, n-pentyl, n-hexyl, eicosyl and the like for alkyls; allyl, 2-butenyl, 3-butenyl, 4-pentenyl, 4-hexenyl, 5Z, 8Z, 11Z, 14Z-eicosatetraenyl and the like as alkenyls.

Examples of $R^2$ in the group $-(CH_2)_n-Z-R^2$ include, for instance,

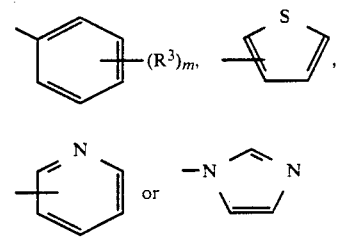

and the like; wherein $R^3$ is hydroxy, lower alkoxy or halogen atom; m is 0 or an integer of 1 to 3.

The compounds of the present invention may be synthesized by the methods explained below.

As the first step an alcohol that is commercially available or has been prepared by means of a conventional method and that has the general formula (II):

wherein $R^1$ has the meaning given above, is protected as necessary if $R^1$ contains functional groups and is then condensed with cyanoacetic acid by a condensing reagent such as 1-ethyl-3-(3-dimethylaminopropyl)carbodiimide in the presence of a base such as 4-dimethylaminopyridine, pyridine or piperidine in an inert solvent such as N,N-dimethylformamide to obtain an ester of cyanoacetic acid of the general formula (III):

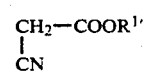

wherein $R^{1'}$ is $R^1$ as defined above or $R^1$ with protected substituents.

The cyanoacetic acid ester (III) obtained from the foregoing step is coupled with a derivative of benzaldehyde of the general formula (IV):

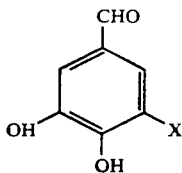
(IV)

wherein X has the meaning given above, in an inert solvent such as benzene or toluene in the presence of a base catalyst such as pyridine or piperidine under the traditional conditions for Knoevenagel condensation and is deprotected by an appropriate method if the substituents in $R^1$ have been protected, whereby a desired derivative of caffeic acid of the general formula (I), is obtained.

Purification of the compounds of the present invention obtained in the above manner is performed by filtering off the precipitated crystalline after cooling the reaction mixture, or by silica gel column chromatography.

Suitable examples of the starting material of the general formula (II) include methanol, ethanol, isopropanol, (5Z,8Z,11Z,14Z)-eicosatetraenol, benzyl alkylene alcohols with or without substituents on the benzene ring, such as phenethyl alcohol, heterocyclic alkylene alcohols, such as 2-(2-thienyl)ethanol, phenyl vinyl alcohols such as 3-phenyl-2-propenol or phenoxy alkylene alcohols such as 2-phenoxyethanol.

The caffeic acid derivatives synthesized may be converted into pharmaceutically acceptable salts thereof as required. For example, sodium, potassium or calcium salts may be used as a medicine.

Since the caffeic acid derivatives of the present invention possess inhibitory activity against 12-lipoxygenase as well as 5-lipoxygenase, they are useful as remedies for circulatory diseases, for example, the prevention of arteriosclerosis.

When applied as remedies for circulatory diseases, the caffeic acid derivatives of the present invention or pharmaceutically permissible salts thereof may be administered orally or parenterally in an appropriate dosage form such as capsule, tablet, or injection, alone or together with known innocuous excipients. For example, these dosage forms may be provided by adopting the following procedures. In order to provide capsules, the original compound is pulverized, mixed with an excipient such as lactose, starch, a derivative thereof or a cellulose derivative, and packed in gelatin capsules. In the case of tablets, a binder such as sodium carboxymethylcellulose, alginic acid or gum arabic and water are added to the compound in addition to the excipient mentioned above, and mixed together by kneading, formed into granules as required, and then a lubricant such as talc or stearic acid is also added. The mixture is formed into tablets using a tablet machine. Injections for parenteral administration are prepared by dissolving the compound of the present invention in sterilized distilled water or sterilized saline together with a solubilizer and packing the solution in sealed ampules. Stabilizers or buffers may be included as required.

Although the effective dose of remedies for circulatory diseases will vary depending on the type and seriousness of the disease, the administration method and the physical condition of the patient, a sufficient amount to suppress the symptoms appearing in the patient is generally administered. As an example, a daily dose of between 1 and 1000 mg is preferable for an adult.

Examples showing the preparation of compounds of the present invention are described below, though the scope of the present invention is not in any way restricted by these specific example.

EXAMPLE 1

Ethyl 2-cyano-3-(3,4-dihydroxyphenyl)-2-propenoate (Compound No. 1)

To a solution of 3,4-dihydroxybenzaldehyde (2.0 g, 14.5 mmol) in ethanol (10 ml) were added ethyl cyanoacetate (1.6 g, 14.5 mmol) and piperidine (3 drops) and the resulting reaction was allowed to proceed for 20 hours at room temperature. Water was then added to the reaction mixture, and the precipitated crystalline was filtered off and recrystallized from ethanol-water to yield the titled compound (2.3 g, 9.9 mmol). Alternatively, the reaction may be conducted in a benzene solution under refluxing conditions. Compound Nos. 2 to 6 were provided in a similar manner.

Compound No. 2: 2-cyano-3-(3,4-dihydroxyphenyl)-2-propenoic acid

Compound No. 3: ethyl 2-cyano-3-(3,4,5-trihydroxyphenyl)-2-propenoate

Compound No. 4: 2-cyano-3-(3,4,5-trihydroxyphenyl)-2-propenoic acid

Compound No. 5: methyl 2-cyano-3-(3,4-dihydroxyphenyl)-2-propenoate

Compound No. 6: isopropyl 2-cyano-3-(3,4-dihydroxyphenyl)-2-propenoate

EXAMPLE 2

(5Z,8Z,11Z,14Z)-eicosatetraenyl-2-cyano-3-(3,4-dihydroxyphenyl)-2-propenoate (Compound No. 7)

Lithium aluminum hydride (90 mg, 2.4 mmol) was suspended in anhydrous tetrahydrofuran (40 ml) and the suspension was cooled to 0° C. under a stream of nitrogen. Then a solution of arachidonic acid (600 mg, 2.0 mmol) in anhydrous tetrahydrofuran (35 ml) was added dropwise to the above suspension under cooling and stirring. The reaction mixture was stirred for 1 hour at 0° C. and then for 1 hour at room temperature. After slow addition of water (0.1 ml), a 10% aqueous solution of sodium hydroxide (0.1 ml) and water (0.3 ml) were further added and the mixture was allowed to stand for 1 hour. Drying the mixture over anhydrous magnesium sulfate followed by concentration in vacuo afforded (5Z,8Z,11Z,14Z)-eicosatetraenol (510 mg, 1.8 mmol).

The above product was dissolved in N,N-dimethylformamide (hereinafter abbreviated as DMF) (10 ml) and cooled to 0° C. Cyanoacetic acid (150 mg, 1.8 mmol) in DMF (4 ml), 1-ethyl-3-(3-dimethylaminopropyl)carbodiimide (273 mg, 1.8 mmol) in DMF (2 ml) and 4-dimethylaminopyridine (21 mg, 0.2 mmol) in DMF (2 ml) were successively added to the solution under cooling and stirring and the mixture was stirred for 1 hour at 0° C. and for a further 3 hours at room temperature. Then the reaction mixture was concentrated in vacuo and extracted with diethyl ether after the addition of water. The organic layer was dried over anhydrous magnesium sulfate, concentrated in vacuo and purified by column chromatography to give (5Z,8Z,11Z,14Z)-eicosatetraenyl cyanoacetate (300 mg, 0.8 mmol).

To a benzene solution (10 ml) of the product thus obtained was added 3,4-dihydroxybenzaldehyde (116 mg, 0.8 mmol) in diethyl ether (10 ml) and piperidine (1 drop) and the whole mixture was refluxed for 1.5 hours with continuous removal of water. The reaction mixture was cooled and concentrated in vacuo to obtain the titled compound (240 mg, 0.5 mmol).

Eicosyl 2-cyano-3-(3,4-dihydroxphenyl)-2-propenoate (Compound No. 8) was synthesized in a similar manner by replacing arachidonic acid with arachic acid.

EXAMPLE 3

Phenethyl 2-cyano-3-(3,4-dihydroxyphenyl)-2-propenoate (Compound No. 9)

To a solution of β-phenethyl alcohol (3.6 ml, 30.0 mmol) in DMF (30 ml) was added cyanoacetic acid (2.55 g, 30.0 mmol) in DMF (20 ml) and the whole was cooled to 0° C. 1-Ethyl-3-(3-dimethylaminopropyl)carbodiimido (4.66 g, 30.0 mmol) in DMF (5 ml) and 4-dimethylaminopyridine (0.37 g, 3.0 mmol) in DMF (10 ml) were then added to the mixture in that order at 0° C. and stirring was continued for 1 hour at this temperature and 18 hours at room temperature. The reaction mixture was concentrated in vacuo and purified by column chromatography to afford phenethyl cyanoacetate (2.49 g, 13.2 mmol).

To a solution of 3,4-dihydroxybenzaldehyde (1.73 g, 12.5 mmol) in DMF (3 ml) was added benzene (30 ml), a portion of the phenyl cyanoacetate obtained above (2.49 g, 13.2 mmol) and benzene (70 ml) in that order and the whole was well mixed. Piperidine (3 drops) was added to the solution and the mixture was refluxed for 2 hours with continuous removal of water using Dean-Stark equipment. Then the reaction mixture was cooled down and concentrated in vacuo. Water was added to the concentrate and the precipitated crystalline was filtered off. The crude product thus obtained was recrystallized from ethanol-water to give the titled compound (3.5 g, 11.3 mmol).

The following compounds were provided in a similar manner by replacing β-phenethyl alcohol with 3-phenyl-1-propanol, 4-phenyl-1-butanol, 5-phenyl-1-pentanol, 4-methoxyphenethyl alcohol, 2-methoxyphenethyl alcohol, 2-(2-thienyl)ethanol, 3-(3-pyridyl)-1-propanol, 3-phenyl-2-propenol, 2-phenoxyethanol, 8-(1-imidazolyl)-1-octanol (e.g. as synthesized according to Japanese Patent Laid-Open No. 112862/1979), respectively:

Phenylpropyl 2-cyano-3-(3,4-dihydroxyphenyl)-2-propenoate (Compound 10)
Phenylbutyl 2-cyano-3-(3,4-dihydroxyphenyl)-2-propenoate (Compound 11)
Phenylpentyl 2-cyano-3-(3,4-dihydroxyphenyl)-2-propenoate (Compound 12)
4-Methoxyphenethyl 2-cyano-3-(3,4-dihydroxyphenyl)-2-propenoate (Compound 13)
2-Methoxyphenethyl 2-cyano-3-(3,4-dihydroxyphenyl)-2-propenoate (Compound 14)
2-(2-Thienyl)ethyl 2-cyano-3-(3,4-dihydroxyphenyl)-2-propenoate (Compound 15)
3-(3-Pyridyl)propyl 2-cyano-3-(3,4-dihydroxyphenyl)-2-propenoate (Compound 16)
3-Phenyl-2-propenyl 2-cyano-3-(3,4-dihydroxyphenyl)-2-propenoate (Compound 17)
2-Phenoxyethyl 2-cyano-3-(3,4-dihydroxyphenyl)-2-propenoate (Compound 18)
8-(1-Imidazolyl)octyl 2-cyano-3-(3,4-dihydroxyphenyl)-2-propenoate (Compound 19)

The compounds with hydroxy substituent(s) on their aromatic rings can be synthesized as follows.

After the protection of phenolic hydroxyl of 4-hydroxyphenethyl alcohol by the formulation of chlorodimethylether, the protected compound was condensed with cyanoacetic acid according to the procedure in Example 1. Further condensation of the product with 3,4-dihydroxybenzaldehyde followed by deprotection in the usual manner provided the following compound.

4-Hydroxyphenethyl 2-cyano-3-(3,4-dihydroxyphenyl)-2-propenoate (Compound 20)

After the reduction of 3,4-dimethoxycinnamic acid to 3-(3,4-dimethoxyphenyl)propanol in the usual manner followed by condensation with cyanoacetic acid according to the procedure in Example 3, the product was demethylated with boron trichloride and condensed with 3,4-dihydroxybenzaldehyde to give the following compound.

3-(3,4-Dihydroxyphenyl)propyl 2-cyano-3-(3,4-dihydroxyphenyl)-2-propenoate (Compound 21)

On the other hand, phenethyl 2-cyano-3-(3,4,5-trihydroxyphenyl)-2-propenoate (Compound No. 22) was obtained by replacing 3,4-dihydroxybenzaldehyde with 3,4,5-trihydroxybenzaldehyde and following the procedure in Example 1.

Physical data in respect of the synthesized compounds Nos. 1 to 22 are shown in Table 1.

TABLE 1

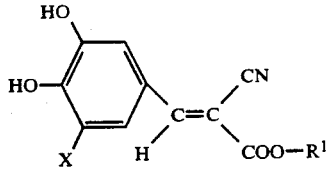

| Compound No. | X | R¹ | Appearance | m.p. (°C.) | Recrystallized from | IR spectrum ($\nu\ cm^{-1}$) (nujol) | NMR spectrum (δ ppm) (270 MHz) (CD$_3$OD) |
|---|---|---|---|---|---|---|---|
| 1 | H | C$_2$H$_5$ | yellow crystalline | 169-170 | EtOH/water | 1700, 2230 | 1.36(3H, t, J=7Hz), 4.33(2H, q, J=7Hz), 6.86(1H, d, J=9Hz), 7.37(1H, dd, J=2Hz, J=9Hz), 7.64(1H, d, J=2Hz), |

TABLE 1-continued

| | | | | | | | |
|---|---|---|---|---|---|---|---|
| 2 | H | H | yellow crystalline | 220 | water | 1680, 2230 | 6.89(1H, d, J=8Hz), 7.38(1H, dd, J=2Hz, J=8Hz), 7.63(1H, d, J=2Hz), 8.10(1H, s) |
| 3 | OH | C₂H₅ | yellow needle | 187 | EtOH/water | 1695, 2230 | 1.35(3H, t, J=7Hz), 4.32(2H, q, J=7Hz), 7.13(2H, s), 8.01(1H, s) |
| 4 | OH | H | yellow needle | 213–215 | EtOH/water | 1690, 2230 | 7.10(2H, s), 7.98(1H, s) |
| 5 | H | CH₃ | yellow needle | 200–204 | MeOH/water | 1695, 2230 | 3.87(3H, s), 6.87(1H, d, J=8Hz), 7.37(1H, dd, J=2Hz, J=8Hz), 7.64(1H, d, J=2Hz), 8.11(1H, s) |
| 6 | H | CH—CH₃ \| CH₃ | pale yellow needle | 119–120 | iso-propanol | 1715, 2240 | 1.34(6H, d, J=6Hz), 5.1–5.2(1H, m), 6.86(1H, d, J=9Hz), 7.37(1H, dd, J=2Hz, J=9Hz), 7.64(1H, d, J=2Hz), 8.08(1H, s) |
| 7 | H | (C18 polyunsaturated chain) | oil | — | | 1720, 2225 *(CHCl₃) | 0.89(3H, t, J=7Hz), 1.2–2.2(14H, m), 2.8–2.9(6H, m), 4.30(2H, t, J=7Hz), 5.3–5.5(8H, m), 6.95(1H, d, J=8Hz), 7.28(1H, dd, J=2Hz, J=8Hz), 7.85(1H, d, J=2Hz), 8.11(1H, s) *(CDCl₃) |
| 8 | H | (long alkyl chain) | yellow crystalline | 123–124 | EtOH | 1735, 2240 | 0.89(3H, t, J=7Hz), 1.2–1.5(34H, m), 1.7–1.8(2H, m), 4.27(2H, t, J=6Hz), 6.86(1H, d, J=9Hz), 7.38(1H, dd, J=1Hz, J=9Hz), 7.64(1H, d, J=1Hz), 8.09(1H, s) |

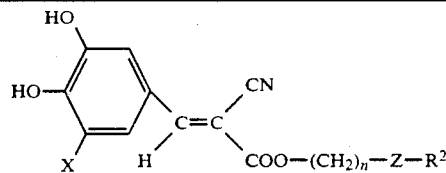

| Compound No. | X | R¹ n | R¹ Z | R² | Appearance | m.p. (°C.) | Recrystallized from | IR spectrum (ν cm⁻¹) (nujol) | NMR spectrum (δ ppm) (270 MHz) (CD₃OD) |
|---|---|---|---|---|---|---|---|---|---|
| 9 | H | 2 | single bond | phenyl | yellow crystalline | 171–172 | EtOH/water | 1730 2230 | 3.03(2H, t, J=7Hz), 4.45 (2H, t, J=7Hz), 6.86(1H, d, J=9Hz), 7.15–7.39(6H, m) 7.63(1H, d, J=2Hz), 8.05(1H, s), |
| 10 | H | 3 | single bond | phenyl | yellow crystalline | 170–173 | MeOH/CHCl₃ | 1690 2225 | 1.92–2.15(2H, m), 2.77 (2H, t, J=7Hz), 4.26(2H, t, J=7Hz), 6.83(1H, d, J=9Hz), 7.10–7.32 (5H, m), 7.36(1H, dd, J=9Hz, 2Hz), 7.65(1H, d, J=2Hz), 8.04(1H, s) |
| 11 | H | 4 | single bond | phenyl | pale yellow crystalline | 149–151 | CHCl₃ | 1700 2225 | 1.60–1.85(4H, m), 2.55–2.77(2H, m), 4.18–4.39(2H, m), 6.85 (1H, d, J=9Hz), 7.08–7.30(5H, m), 7.37(1H, dd, J=9Hz, 2Hz), 7.65(1H, d, J=2Hz), 8.08(1H, s) |
| 12 | H | 5 | single bond | phenyl | yellow crystalline | 144–146 | benzene | 1690 2225 | 1.35–1.55(2H, m), 1.55–1.83(4H, m), 2.64(2H, t, J=8Hz), 4.27 (2H, t, J=7Hz), 6.84(1H, d, J=8Hz), 7.05–7.28(5H, m), 7.35(1H, dd, J=9Hz, 2Hz), 7.65(1H, d, J=2Hz), 8.06(1H, s) |

TABLE 1-continued

| No. | R | n | Linker | Ar | Appearance | mp (°C) | Solvent | IR | NMR |
|---|---|---|---|---|---|---|---|---|---|
| 13 | H | 2 | single bond | 4-OCH₃-C₆H₄— | yellow crystalline | 194–198 | EtOH/water | 1680 2210 | 2.96(2H, t, J=7Hz), 3.76(3H, s), 4.40(2H, t, J=7Hz), 6.84 (1H, d, J=9Hz), 6.86(2H, d, J=9Hz), 7.21(2H, d, J=9Hz), 7.34(1H, dd, J=9Hz, 2Hz), 7.63(1H, d, J=2Hz), 8.04(1H, s) |
| 14 | H | 2 | single bond | 2-CH₃O-C₆H₄— | yellow crystalline | 157–160 | EtOH/water | 1725 2240 | 3.04(2H, t, J=7Hz), 3.83(3H, s), 4.42(2H, t, J=7Hz), 6.78–6.97(3H, m), 7.15–7.28(2H, m), 7.34(1H, dd, J=9Hz, 2Hz), 7.62(1H, d, J=2Hz), 8.00(1H, s) |
| 15 | H | 2 | single bond | 2-thienyl | yellow crystalline | 168–170 | EtOH/water | 1680 2220 | 3.27(2H, t, J=7Hz), 4.45 (2H, t, J=7Hz), 6.83(1H, d, J=9Hz), 6.88–6.99(2H, m), 7.18–7.27(1H, m), 7.35(1H, dd, J=8Hz, 2Hz), 7.65(1H, d, J=2Hz), 8.08(1H, s) |
| 16 | H | 3 | single bond | 3-pyridyl | yellow crystalline | 174–177 | EtOH/water | 1710 2200 | 2.02–2.16(2H, m), 2.84 (2H, t, J=7Hz), 4.30(2H, t, J=7Hz), 6.84(1H, d, J=8Hz), 7.31–7.48 (2H, m) 7.65(1H, d, J=1Hz), 7.77(1H, d, J=8Hz), 8.04(1H, s), 8.33–8.40(1H, m) 8.45(1H, d, J=1Hz) |
| 17 | H | 1 | —CH=CH— | C₆H₅— | yellow crystalline | 171–174 | EtOH/water | 1695 2200 | 4.93(2H, d, J=6Hz) 6.33–6.48(1H, m), 6.69–6.88(2H, m), 7.20–7.48(6H, m), 7.67(1H, d, J=2Hz), 8.13(1H, s) |
| 18 | H | 2 | —O— | C₆H₅— | yellow crystalline | 186–189 | EtOH/water | 1720 2220 | 4.30(2H, t, J=5Hz), 4.60 (2H, t, J=5Hz), 6.84(1H, d, J=9Hz), 6.85–6.98(3H, m), 7.20–7.33(2H, m), 7.36(1H, dd, J=9Hz, 2Hz), 7.65(1H, d, J=2Hz), 8.09(1H, s) |
| 19 | H | 8 | single bond | imidazolyl | yellow crystalline | 184–186 | MeOH | 1720 2210 | 1.18–1.52(8H, m), 1.61–1.87(4H, m), 4.01(2H, t, J=7Hz), 4.26(2H, t, J=7Hz), 6.87(1H, d, J=9Hz), 6.95(1H, brs), 7.11(1H, brs), 7.38(1H, d, J=7Hz), 7.65(2H, brs), 8.09(1H, s) |
| 20 | H | 2 | single bond | 4-OH-C₆H₄— | yellow crystalline | 186–189 | ethyl acetate/ hexane | 1725 2225 | 2.93(2H, t, J=7Hz), 4.39 (2H, t, J=7Hz), 6.72(2H, d, J=9Hz), 6.85(1H, d, J=8Hz), 7.11(2H, d, J=9Hz), 7.35(1H, dd, J=8Hz, 2Hz), 7.64(1H, d, J=2Hz), 8.05(1H, s) |
| 21 | H | 3 | single bond | 3,4-(OH)₂-C₆H₃— | yellow crystalline | 172–176 | EtOH/water | 1695 2220 | 1.82–2.07(2H, m), 2.62 (2H, t, J=6Hz), 4.24(2H, t, J=6Hz), 6.53(1H, dd, J=9Hz, 2Hz), 6.58–6.72 (2H, m), 6.87(1H, d, J=9Hz), 7.37(1H, dd, J=9Hz, 2Hz), 7.66(1H, d, J=2Hz), 8.06(1H, s) |
| 22 | OH | 2 | single bond | C₆H₅— | yellow crystalline | 170–172 | EtOH/water | 1690 2220 | 3.03(2H, t, J=7Hz), 4.44(2H, t, J=7Hz), 7.12(2H, s) 7.15–7.38(5H, m), 7.99(1H, s) |

Examples of formulation are shown below.

| Formulation 1 (capsules) | |
|---|---|
| Compound No. 1 | 10 g |
| Lactose | 30 g |
| Corn starch | 30 g |
| Crystallinecellulose | 28 g |
| Magnesium stearate | 2 g |
| Total | 100 g |

The above mixture was formed into granules in the usual manner and packed in 200 hard gelatin capsules. Each capsule thus obtained contains 50 mg of the active ingredient.

| Formulation 2 (tablets) | |
|---|---|
| Compound No. 9 | 20 g |
| Lactose | 40 g |
| Corn starch | 20 g |
| Hydroxypropylcellulose | 18 g |
| Talc | 2 g |
| Total | 100 g |

The above mixture was blended in a mixer and formed into 200 tablets of 500 mg each. Each tablet thus obtained contains 200 mg of the active ingredient.

EXAMPLES OF PHARMACOLOGICAL TESTS

The 12-lipoxygenase inhibitory activity of the compounds of the present invention was measured by conducting the three types of pharmacological tests described below.

METHOD 1

Citrated blood was collected from the abdominal aorta of a rat. Washed platelet was prepared in the usual way, diluted with phosphate buffer (pH=8.0) containing 0.45% NaCl and used as the enzyme solution. To the solution were added the sample compound (10 μM), [$^{14}$C]arachidonic acid (0.2 μCi) and arachidonic acid (3 μg) and the mixture was reacted for 3 to 5 minutes at 37° C. The reaction mixture was developed by thin layer chromatography and 12-HETE was identified by a radio chromato scanner. The reduction in 12-HETE production which resulted was used as the index of 12-lipoxygenase inhibitory activity.

METHOD 2

Citrated blood was collected from the heart of a rat and platelet-rich plasma was prepared in the usual way. The plasma was washed twice with isotonic buffer solution (A) [134 mM NaCl, 5 mM D-glucose, 1 mM EDTA, 1 mM EGTA, 15 mM Tris-HCl (pH=7.4)], frozen and stored at −80° C. It was thawed before use, ultrasonified in ice water and used as the enzyme solution. To the isotonic buffer solution (A) were added 1 mM GSH, the sample compound (final concentration: 1 μM) and the enzyme solution (300 to 500 μg protein) and the mixture was pre-incubated for 5 minutes at 37° C.; then [$^{14}$C]arachidonic acid (0.05 μCi) (final concentration: 4.3 μM) was further added and reacted for 5 minutes. After the reaction had been quenched, the reaction mixture was developed on a silica gel thin layer plate and 12-HETE was identified by autoradiography. The reduction in 12-HETE production was used as the index of 12-lipoxygenase inhibitory activity.

METHOD 3

The platelet-rich plasma obtained in the same way as described in Method 2 was washed successively with isotonic buffer solution (A) and isotonic buffer solution (B) [134 mM NaCl, 5 mM D-glucose, 0.1 mM DETA, 0.1 mM EGTA, 15 mM Tris-HCl (pH=7.4)] in that order, and suspended in a hypotonic buffer solution (C) [25 mM Tris-HCl (pH=7.7)]. The suspension was treated by a "freeze-thaw" procedure three times and centrifuged at 10500× g for 60 minutes. An aliquot of the supernatant (platelet soluble fraction) was used as the enzyme solution. To the hypotonic buffer solution (C) were added 1 mM GSH, [$^{14}$C]arachidonic acid (0.025 μCi) (final concentration: 40 μM), the sample compound (final concentration: 10 μM) and the enzyme solution (50 μg protein) and the mixture was reacted for 5 minutes at 37° C. The index of 12-lipoxygenase inhibitory activity was obtained in the same way as described in Method 2.

RESULTS

The production indexes of 12-HETE under the inhibitory influence of the compounds of the present invention are shown in Table 2, where the production amount of the control experiment (in the absence of the sample compound) is 100%.

TABLE 2

| Compound No. | Method 1 (%) | Method 2 (%) | Method 3 (%) |
|---|---|---|---|
| 1 | 38.1 | | |
| 5 | 36.0 | | |
| 6 | 31.4 | | |
| 9 | | 10.0 | 25.1 |
| 10 | | 12.1 | |
| 11 | | 14.2 | |
| 13 | | | 19.5 |
| 14 | | | 19.1 |
| 15 | | 8.7 | |
| 17 | | 13.2 | |
| 18 | | 8.5 | |
| Baicalein (for comparison) | 27.0 | 9.8 | 22.7 |

Since caffeic acid derivatives of the present invention exhibit 12-lipoxygenase inhibitory activity, they are useful for the prevention and remedy of circulatory diseases such as arteriosclerosis. The caffeic acid derivatives of the present invention can be easily made by synthesis.

What is claimed is:

1. A caffeic acid derivative of the general formula (I) and pharmaceutically permissible salts thereof:

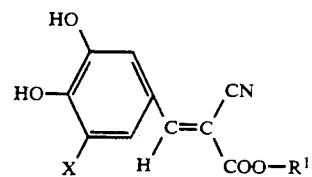

wherein X is a hydrogen atom or hydroxy group; R' is a straight or branched chain alkyl or an alkenyl group wherein said alkyl or alkenyl groups contain up to 20 carbon atoms or a group of the formula:

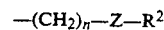

wherein n is an integer of 1 to 10; Z is an oxygen atom, a vinylene residue or a single bond, and $R^2$ is selected from

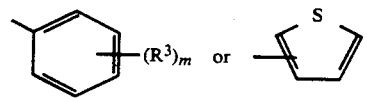

wherein $R^3$ is selected from hydroxy groups, lower alkoxy groups and halogens and m is an integer from 0 to 3.

2. A caffeic acid derivative of the general formula (II) and pharmaceutically acceptable salts thereof:

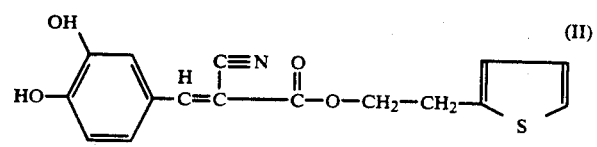

3. A pharmaceutical composition used as a remedy for circulatory diseases which comprises a pharmaceutically effective amount of a compound of claim 1 together with a pharmaceutically acceptable carrier.

4. A method for inhibiting arteriosclerosis which comprises administering to a patient a sufficient amount of a caffeic acid derivative as defined by claim 1 to suppress symptoms of arteriosclerosis appearing in said patient.

5. A method according to claim 4 wherein said derivative is administered in a daily dosage of between 1 and 1000 mg.

* * * * *